(12) United States Patent
Kritchman et al.

(10) Patent No.: US 6,784,994 B1
(45) Date of Patent: Aug. 31, 2004

(54) SYSTEM AND METHOD FOR ACCURATELY REPRODUCING COLOR

(75) Inventors: Eli Kritchman, Tel-Aviv (IL); Jeffrey Steinhauer, Rehovot (IL); Michael Shuster, Tel-Aviv (IL)

(73) Assignee: Hewlett-Packard Indigo B.V., Maastricht (NL)

( * ) Notice: Subject to any disclaimer, the term of this patent is extended or adjusted under 35 U.S.C. 154(b) by 0 days.

(21) Appl. No.: 10/070,237
(22) PCT Filed: Sep. 1, 1999
(86) PCT No.: PCT/IL99/00476
§ 371 (c)(1), (2), (4) Date: Feb. 28, 2002
(87) PCT Pub. No.: WO01/16567
PCT Pub. Date: Mar. 8, 2001

(51) Int. Cl.$^7$ .................................................. G01J 3/46
(52) U.S. Cl. .................................................... 356/402
(58) Field of Search ............................. 356/402, 446; 358/500, 501, 504

(56) References Cited

U.S. PATENT DOCUMENTS 5,003,500 A    3/1991   Gerber

FOREIGN PATENT DOCUMENTS

| DE | 32 21 812 | 1/1983 |
| EP | 0 065 484 | 11/1982 |
| EP | 0 669 754 | 8/1995 |
| WO | WO 98/46008 | 10/1998 |

*Primary Examiner*—F. L. Evans
(74) *Attorney, Agent, or Firm*—Fenster & Company

(57) ABSTRACT

A method of determining an adjusted color to be used for computing colorants for printing on a specified substrate, comprising: specifying an apparent color; estimating diffuse reflection from an outside surface of colorants when printed on the specified substrate; and adjusting the specified color for the effects of the estimated diffuse reflection to determine a color to be used for computing the colorants.

10 Claims, 3 Drawing Sheets

US 6,784,994 B1

SYSTEM AND METHOD FOR ACCURATELY REPRODUCING COLOR

RELATED APPLICATIONS

The present application is US national application of PCT/IL99/00476, 1 Sep. 1999.

FIELD OF THE INVENTION

The present invention relates to color printing and copying, and more particularly to accurately reproducing and measuring color regardless of the substrate on which it is produced.

BACKGROUND OF THE INVENTION

In order to reproduce color prints such as for printing, photography or copying, the spectrum of light that emerges from the printed colors is determined. The print is illuminated and the reflected light emerging therefrom is detected. A portion of the light directed to the surfaces of the print is absorbed and a certain amount of the light is transmitted through the colorant and reflected back through the colorant by the substrate. In the prior art, measurements are made of the spectral distribution of the illuminant (or more precisely of the reflection from an unprinted substrate), and the spectral reflectance of the printed substrate. The difference is assumed to be due to absorption by the colorant on the substrate.

However, in addition to the effect of the color of the substrate, it is known that the final apparent color of a print also depends on other characteristics of the substrate on which the color is printed or spread. This is true whether the color data for printing is computer generated or generated by scanning a physical image. Thus, when copies are made on both glossy and matte substrates, with the same colorant thickness, their apparent color is different.

Another problem in the printing field is matching the OD of a printed color with some desired value of color. In general, as the color saturation increases reflective methods become less sensitive and less accurate.

FIG. 1 illustrates a standard apparatus and methodology for measuring colors printed on a sheet. A light source 12 illuminates a sheet having a colored layer 14 printed on a sheet 16 at some angle to the normal to the sheet. A detector 18 which views the surface generally from a direction normal to the surface, receives light which passes through layer 14 and which is diffusely reflected 13 from the surface of sheet 16. Light source 12 is set at an angle so as to avoid specular reflection from the surface of color layer from affecting the color measurement. Diffuse reflection 15 from the surface of color layer 14, does affect the measurement. However, this measurement of the diffuse reflection mimics the apparent optical density seen by an observer, since the observer also views this diffusely reflected light. A series of filters is used to separate the color reaching the detector into spectral components, which breakdown is used to determine the apparent OD of each of the process colors required to reproduce the color or to enable preparation of a specially mixed color.

When the OD of a single patch of process or specially mixed color is being measured, a series of filters are sequentially placed between sheet 16 and detector 18. Each of these filters corresponds to one of the process colors and selectively passes the spectral band absorbed by that process color. The identity of the process color being tested can be determined from the filter which gives the lowest output for detector 18. The OD is determined from the amplitude of the light which reaches the detector with the color filter associated with the particular process color. Here again, the effects of specular reflection from the colored layer is avoided, but there is an effect of the diffuse reflection therefrom on the measurement. Of course, if the identity color being measured is known, a priori, as in an in-line densitometer, the measurement may be made immediately with the correct filter.

SUMMARY OF THE INVENTION

An aspect of some preferred embodiments of the invention is related to more accurate production of printed images, independently of the gloss of the substrate on which the images are being printed.

An aspect of some preferred embodiments of the invention is related to more accurate copying of printed images, while reducing the effect of gloss from the color accuracy.

An aspect of some preferred embodiments of the invention relates to compensation for the characteristics of the surface being printed upon.

In general, if the apparatus of FIG. 1 is used to measure the color spectrum of the colors of the printed surface and this measured spectrum is used to compute the percentage of coverage of primary colors for printing, or the color components used to mix a special color, the printed image will have a somewhat different color than that of the original image. Furthermore, this effect will depend on the finish of the master image and of the copy, and may exist even if the master and the copy have the same finish.

In accordance with a preferred embodiment of the invention, the effect of diffuse reflection from the surface of a color layer is separated from the effect of light that is diffusely reflected from the substrate after passing the color layer by which the color is printed or otherwise formed. The two components are preferably separately taken into account for both measurement purposes and for computation of the amounts of color that are to be printed (either as process colors or as color components of a special colorant), to achieve a required apparent color and optical density (OD).

In a preferred embodiment of the invention, a value "S" is determined that is dependent primarily on the gloss of the print. This factor corresponds to the diffuse light that is reflected from the surface of the color layer. In general it can be considered to be equal to the ratio of the light measured from the printed substrate and the light measured from the underlying unprinted substrate. The glossier the print (often directly related to the gloss of the underlying substrate) the smaller S, since for glossy prints the specular reflection is high, but the diffuse reflection is low. The gloss of the print closely relates to the gloss of the substrate because of the relative thinness of the printed ink, especially for liquid inks and toners.

In a preferred embodiment of the present invention, to determine S, any color is thickly printed on a substrate. Preferably, the ink thickness is such that the diffused scatter from the surface of the printed color, in the wavelength band in which the color absorbs light, is much larger than the light that passes through the color layer, strikes the substrate and is reflected back to the detector or light sensor. A filter, which limits the light measured by the detector to that portion of the spectrum that is absorbed by the color layer, is placed in front of the detector, which in turn, determines the apparent OD.

With no light passing, within the band of the filter, passing through the colorant, the light measured by the detector is substantially only the light that is diffusely reflected from the surface of the colorant. The value S, which can be expected to be the same over the entire spectrum, is calculated from the inverse logarithm to the base 10 of the OD measured through the filter. Even though the scatter is measured only over a limited wavelength band, the value achieved may be assumed to be constant over the entire visible region, since the same scatter mechanism is operative over the entire visible spectrum.

With knowledge of the value of S for prints on the particular substrate, the measured spectrum (or the spectrum computed for a computer image) can be corrected to determine which portion of the desired apparent spectrum must be supplied by light that passes twice through the color layer. Since S will be supplied by the scatter from the surface, the amount to be supplied by the light that passes through the printed colors can be calculated. This correction will apply to whether the color is being reproduced with a series of halftone process color separations or with a single specially formulated colorant.

An aspect of some preferred embodiments of the invention is related to more accurate measurement of color OD of printed substrates.

An aspect of some preferred embodiments of the invention is related to the more accurate determination of the absorption of colored layers, independently of the gloss of the substrate on which the image is formed.

As indicated above, in the normal methodology of measuring the OD of printed surfaces, a filter, which is matched to the maximum absorption band of the particular colorant (ink or toner), is used to filter the light received by the detector. However, for high ODs, the amount of light reflected from the outer surface of the colorant may be as high as that which passes through the colorant. Thus, when the measurements determine a lower than desired OD, an operator can not overcome this situation by increasing the thickness of the colorant.

Some preferred embodiments of the invention are meant to solve or reduce the effects of saturation on the measurement of OD of a printed patch of a given process or special color. Such patches are routinely used to determine if a proper thickness of colorant is being applied to the substrate. An operator measures the OD of the color (using the method described in the background) and adjusts the thickness of the colorant (either mechanically or electrically, dependent on the type of printer) to achieve the desired OD. However, when the colorant is near saturation (i.e., so thick that little light passes through it in the spectrum band of maximum absorbance), the measurement is inexact, since the main component measured using a filter which passes only this band, is diffuse reflection from the surface of the printed colorant layer.

In a preferred embodiment of the invention, an "incorrect" filter is used in the measurement of OD, whenever the filter usually used (i.e., that is matched to the colorant) blocks almost all the light that passes through the colorant (i.e., the system is in saturation).

In a preferred embodiment of the invention, for high OD values of a particular process color, the filter for a colorwise adjoining process color is used. Either, the detector system is calibrated to determine the OD of the printed color even though the "incorrect" filter is used or, alternatively, the operator is instructed to use an "incorrect" filter and given a value of OD to aim for, utilizing a detector that is calibrated in the normal manner.

This aspect of the invention can also be applied to the measurement of single color inks. In general such inks have a wide and varying absorption spectrum. Thus, while one portion of the spectrum may be in saturation, other, visually important portions may not be in saturation. If the measurement is made, as is usual, at wavelengths of maximum absorption, the measurement may become insensitive to thickness even though the actual appearance of the colorant layer is still changing substantially with thickness. In accordance with a preferred embodiment of the invention, a filter having a band outside the band of maximum absorption of the colorant is used.

This improved measurement of the quantity of the colorant on the substrate allows for proper coloration for less saturated regions of the spectrum.

There is thus provided, in accordance with a preferred embodiment of the invention, a method of determining an adjusted color to be used for computing colorants for printing on a specified substrate, comprising:

specifying an apparent color;

estimating diffuse reflection from an outside surface of colorants when printed on the specified substrate; and adjusting the specified color for the effects of the estimated diffuse reflection to determine a color to be used for computing the colorants.

In a preferred embodiment of the invention, the specified color is a color spectrum.

In a preferred embodiment of the invention, the specified apparent color is determined from a measurement of a printed exemplar.

Preferably, the method includes determining a mixture of colorants based on the adjusted spectrum. Preferably, the method includes printing the mixture of colorants as separate separations on the substrate. Preferably, the separations are printed as half-tone configurations.

In a preferred embodiment of the invention, the colorants comprise at least one process color.

Preferably, determining the mixture of color components comprises determining a percent coverage of the colorants of the separations on the substrate.

Preferably, the method includes correcting the estimate of diffuse reflection based on a percent coverage of the paper by the colorants and repeating the determination of the color mixture based on the corrected estimate.

In a preferred embodiment of the invention, the method includes printing the mixture of colorants as a single layer of mixed colorant.

There is further provided, in accordance with a preferred embodiment of the invention, a method of determining the OD of a printed colorant, comprising:

determining a visible wavelength region in which the color is at or near saturation; and if a portion of a determination of saturation is found, determining the OD in a wavelength region at which the color is not near saturation.

In a preferred embodiment of the invention, the method includes, if none of the visible wavelength region is at saturation:

determining the OD in a wavelength region at which the spectrum of light reflected from the colorant is a minimum.

Preferably, the method includes acquiring a reflection spectrum of the printed colorant including at least a wavelength region in which the color is not near saturation, wherein the OD is determined based on a reflectance measurement at a wavelength in which the color is not in saturation.

In a preferred embodiment of the invention, determining the OD comprises filtering the reflection through a filter which passes at least a portion of the wavelength region in which the color is not in saturation and measuring the filtered reflection.

There is further provided, in accordance with a preferred embodiment of the invention a method of choosing a filter for performing a preferred method of the invention from a plurality of filters, comprising:

determining which of the filters in the plurality of filters blocks a maximum amount of the reflected light without saturation of the measurement; and utilizing the thus determined filter to filter the reflection prior to measurement.

In a preferred embodiment of the invention, wherein the colorant is a process color and wherein the plurality of filters comprise a filter associated with each of the process colors, each said filter selectively passes only wavelengths for which the colorant has a high absorption and including:

determining which of the filters that do not cause a saturation condition in the measurement of OD, blocks a maximum of the reflected light and utilizing the thus determined filter to filter the reflection prior to measurement.

Preferably, the filter is a filter other than the filter associated with the process color.

There is further provided, in accordance with a preferred embodiment of the invention, a method for determining the diffuse reflection from the surface of a printed colorant comprising;

printing the colorant with a thickness such that the color is saturated in a given wavelength band; and measuring the diffuse reflection of light from the printed colorant in said wavelength band.

Preferably, measuring the diffuse reflection comprises measuring the diffuse reflection of light from the surface through a filter that selectively passes light only in the given wavelength band.

BRIEF DESCRIPTION OF THE DRAWING

The above described, and other objects and features of the present invention will be best understood when considered in light of the following non-limiting description made in conjunction with the accompanying drawings; wherein.

DESCRIPTION OF PREFERRED EMBODIMENTS OF THE INVENTION

Figure 1:
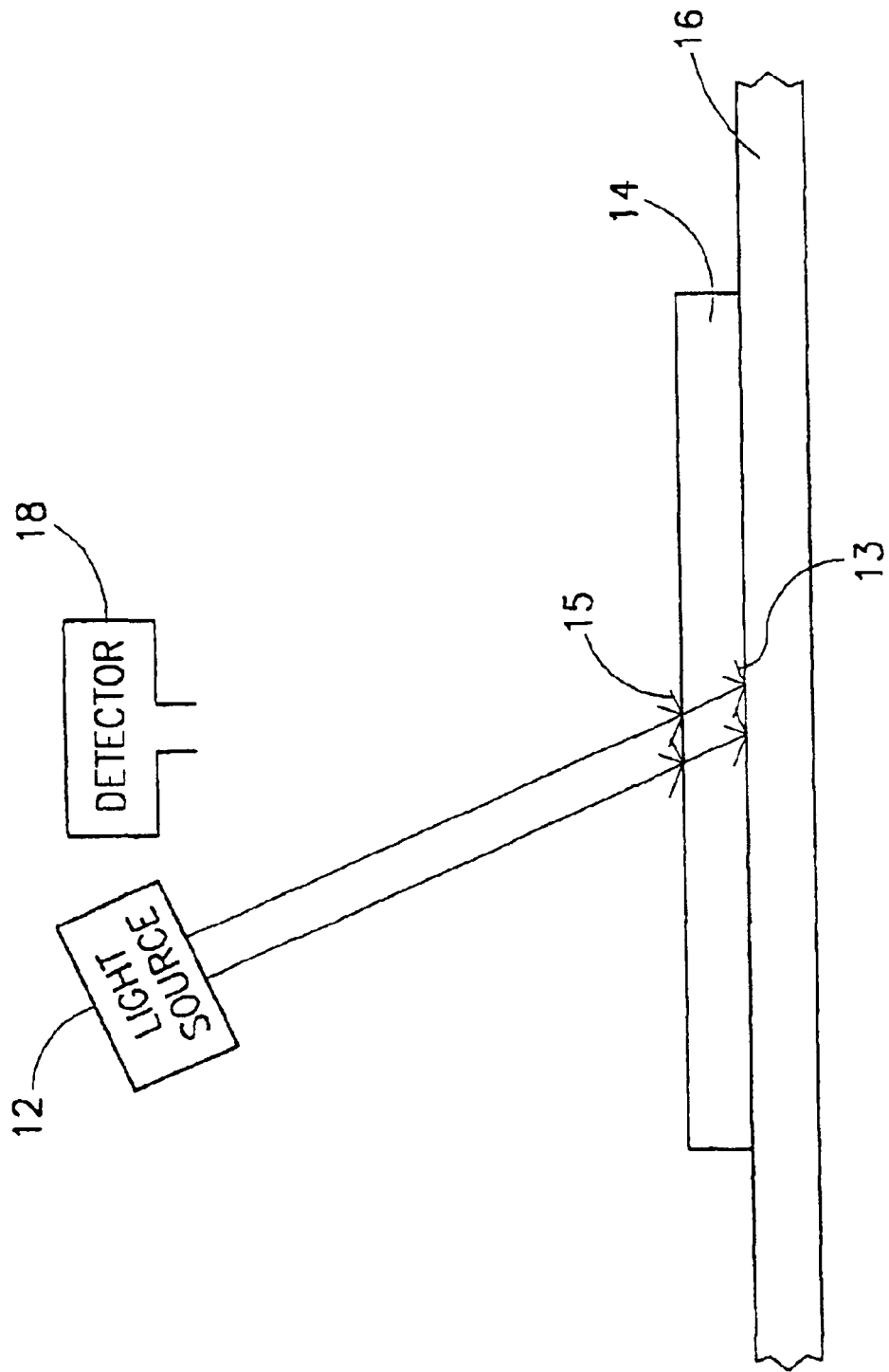
FIG. 1 shows a detector for detecting optical density of printed substrates and for determining the color components of a printed image area.
Figure 2A:
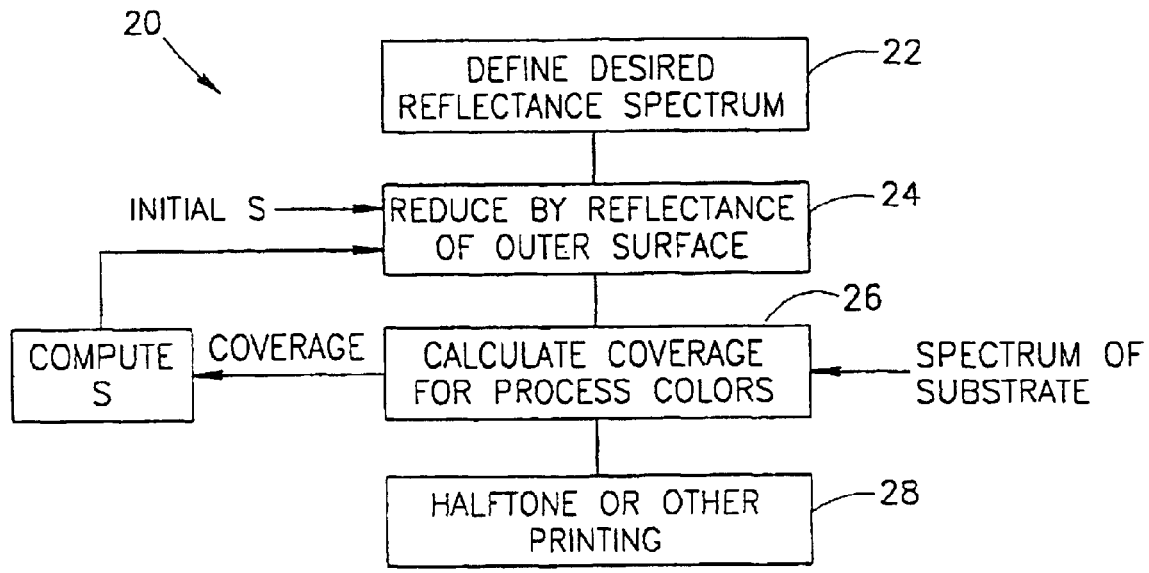
FIG. 2A is a flow chart of a method for determining the correct process colors for printing on a substrate to achieve a desired color spectrum, in accordance with a preferred embodiment of the invention.

FIG. 2A shows a flow chart which outlines a method 20, for determining the correct colors for printing on a substrate to achieve a desired color spectrum, in accordance with a preferred embodiment of the invention. First a desired color reflectance spectrum for the printed area is determined (22). This desired spectrum may be defined by a computer or may be the result of measurement of a sample image whose spectrum is measured in accordance with methods of the prior art, as described, for example with respect to FIG. 1 in the background section hereof. Furthermore, this spectrum may be defined in terms of percent coverage of process color inks or toners. Preferably, for the preferred embodiment of the invention, the actual spectrum is computed or estimated from the coverage percentages.

This desired reflectance spectrum can be considered as being comprised of two parts. One part is the diffuse reflection from the surface of the colorant being printed. A second part is the diffuse reflection from the underlying substrate 16 on which an image is to be printed, either after it passes (twice) through the colorant or in areas for which no colorant is present. The sum of the two diffuse reflections determines the color that will be seen by an observer, assuming there is no specular reflection (glare). Since glare is avoid instinctively by a viewer, this sum is equal to the target reflectance spectrum for printing.

In order to separate the target spectrum into two parts for computation of colorant coverage, the target reflectance spectrum is reduced (24) by the scattered (diffuse) reflectance "S" of a surface colorant as printed on the paper or other substrate on which the image is to be printed. A method of determining this reflectance is described below. An initial value of S based on a value for 100% coverage as derived below, is estimated and then corrected in the manner described below.

The coverage for each of the process colors is then determined (26) in any conventional manner known in the art, utilizing the spectrum as reduced by the reflectance S, rather than the measured or defined reflectances. The usual implicit assumption that the diffuse and specular reflection from the unprinted portions of the paper is the same as for the paper underlying the colorant, is made. The reflectance of the paper or other substrate is most preferably also known/measured, to more precisely determine the proper coverage.

It is assumed that the scattering is a constant fraction s of the incident light and depends on the type of paper (for liquid inks). It may be about 2% for copy paper, which is rough and 0.2% for glossy paper. In effect, it adds a white component to the color. The reflectance of the ink layer then becomes: $\rho(\lambda)=s+(1-s) S(\lambda)\rho_b(\lambda)$, where $S(\lambda)$ is the reflectance of the substrate and $\rho_b(\lambda)$ is the reflectance contributed by the colorant layer itself (assuming no gloss and pure white light and paper). For a given measured or desired apparent reflectance $\rho(\lambda)$, the colorant contribution $\rho_b(\lambda)$, can be computed. By integration over the spectrum (or rather over portions of the spectrum) all the calorimetric parameters, the tristimulus parameters X, Y, Z (or $L^*$, $a^*$, $b^*$) OD etc., can be computed The computed coverage for all of the process colors is computed and sent to circuitry 29 for computing S (which circuitry may be a computer such as the computer or controller of the printer). This circuitry computes the expected overall coverage of all of the half tone separations and, from this coverage, a new value of S for the computation. One or two iterations may be necessary for the value of S to converge. Alternatively this correction may be omitted and a value of S estimated based on the spectrum.

Figure 2B:
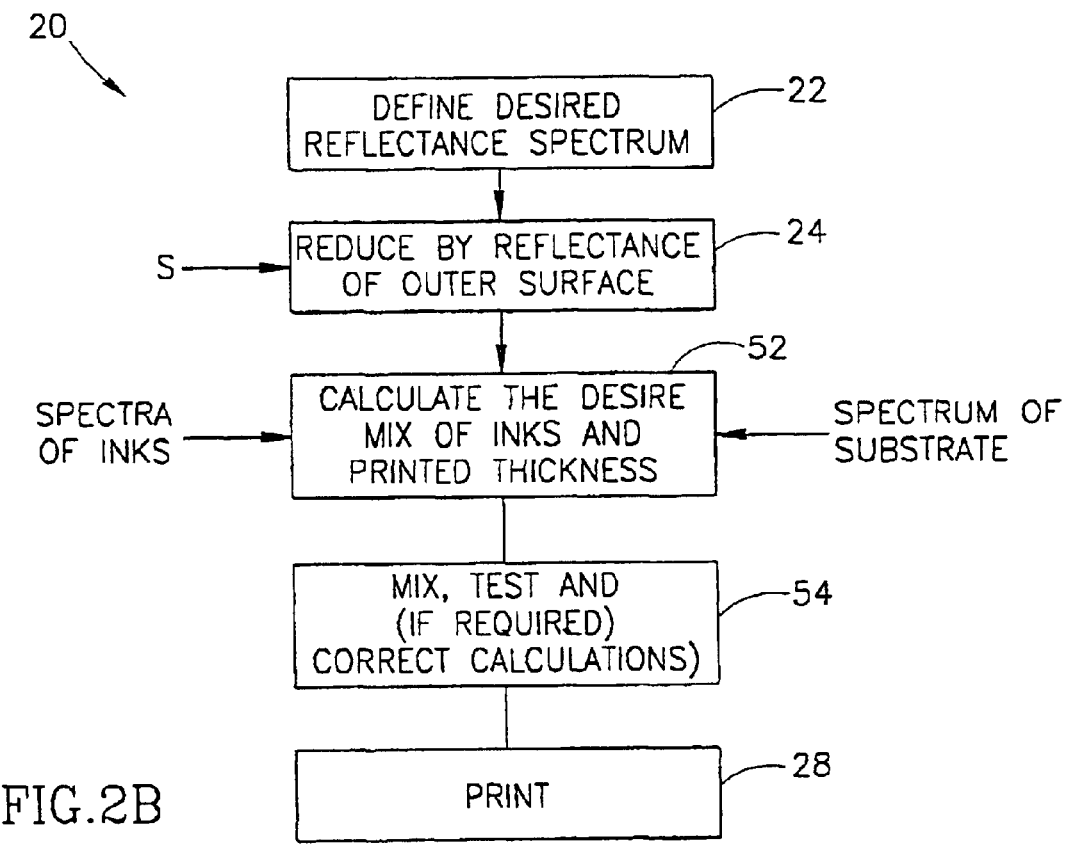
FIG. 2B is a flow chart of a method for determining the correct color mixture for a special colorant for printing on a substrate to achieve a desired color spectrum, in accordance with a preferred embodiment of the invention.

Alternatively, a special colorant is designed to produce the reflection reduced spectrum. FIG. 2B shows, in flow chart form, a method 50 for determining the mixtures of inks to be used. As in method 20, the spectrum is defined and reduced by S (22, 24). Since coverage for such a mix is generally 100%, no correction is necessary for S. However, if the special ink is to be printed in halftone, such correction may be required. To determine the mix of inks and the printing thickness required for the final product (52), the spectra of the inks used for mixing must be known or measured. This ink is then mixed, tested, and if necessary the mix and/or the thickness are (54) adjusted to achieve the desired apparent color.

These colors are then printed (28) in any manner known in the art.

Figure 3:
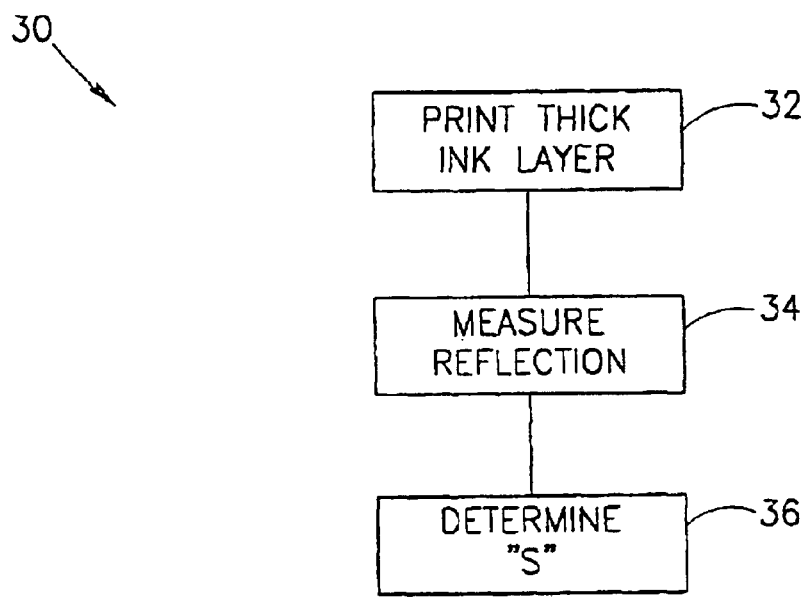
FIG. 3 shows a flow chart of a method of determining the reflectance S, in accordance with a preferred embodiment of the invention.

FIG. 3 shows a flow chart of a method (30) of determining the reflectance S, in accordance with a preferred embodiment of the invention.

A substrate of the type on which the final image is to be printed is printed (32) with a relatively thick layer of one of the colors. The amount of scattered light from the colorant surface does not vary much from one colorant to another within a particular technology. Therefore this test may be performed with any color of colorant, and the measured S applied to all the colors. The printed color should be thick enough such that the amount of light that passes through the layer and is diffusely reflected from the paper (through the layer) to the detector is small, compared to the amount of light diffusely reflected from the surface of the substrate. The reflection from the surface of the colorant is then measured (34), using the conventional methodology (or any other methodology) shown in FIG. 1. If a process colorant is used, then a filter that passes only wavelengths absorbed by the colorant are preferably used. If black colorant is used, any or no filter can be used. If a spectrometer is used, the spectral band of minimum reflectance characterizes S. Since the measured reflection is not dependent on the color, but only on the surface characteristics of the colorant, the reflectance is assumed (unless some variation is known or suspected) to be the same over the entire spectrum.

It should be understood that S need not be measured for each print job, but may be measured once for each combination of colorant type and substrate and used for all subsequent is print jobs.

In most cases the thickness of the colorant is not critical for this measurement. For inks and liquid toners, the colorant is relatively thin and the surface finish of the printed portion is very similar to that of the underlying substrate, for any reasonable colorant thickness. On the other hand, for materials such as powder toner, the image gloss is only weakly dependent on the surface qualities of the underlying substrate. Of course, if the image is treated (as with a gloss enhancing roller) to change its surface gloss, the determination of S should be performed on a test print similarly treated.

Figure 4:
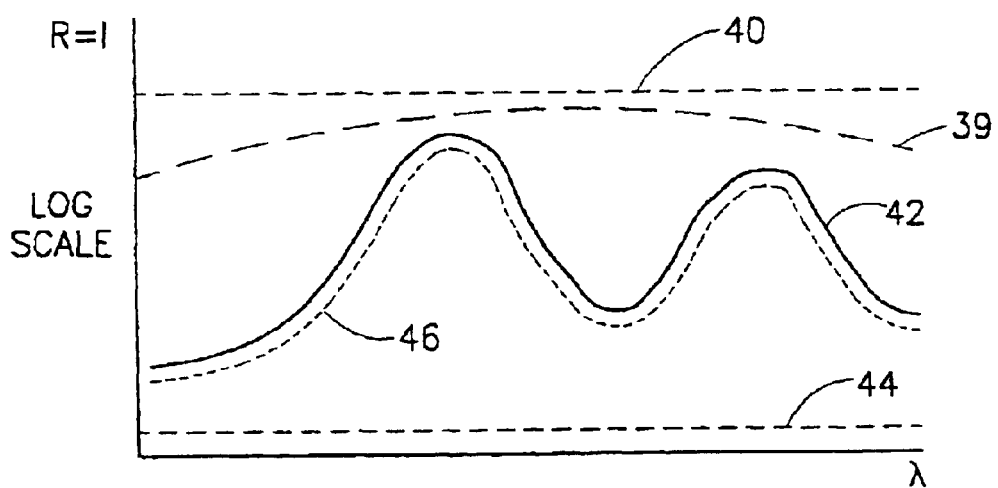
FIG. 4 shows various spectra useful in understanding preferred embodiments of the invention.

FIG. 4 shows the various spectra referred to in the above description. These can be considered as either reflectance spectra "R" or intensity spectra "I". The (diffuse) reflectance spectrum of a "calibration white" (39) substrate is taken as a reference (40). This reference is shown as a straight line, under the assumption that calibration white is "pure white." It is understood that any deviation of the substrate from pure white is preferably compensated for in the usual manner. Reference 42 designates the desired reflectance spectrum on a log scale with respect to the reference. As indicated above, this spectrum may be determined by measurement of an exemplar to be reproduced or by a computer. (Reference 22 of FIG. 2.) Reference 44 designates the diffuse reflectance, S, from the surface of the colorant. (Reference 36 of FIG. 3.) Reference 46 designates the "corrected" spectrum to be used for computing coverage of the ink. (Reference 28 of FIG. 2)

Another aspect of the invention is meant to solve or reduce the effects of saturation on the measurement of OD of a printed patch of a given process or special color. Such patches are routinely used to determine if a proper thickness of colorant is being applied to the substrate. An operator measures the OD of the color (using the method described in the background) and adjusts the thickness of the colorant (either mechanically or electrically, dependent on the type of printer) to achieve the desired OD. However, when the colorant is near saturation (i.e., so thick that little light passes through it in the spectrum band of maximum absorbance), the measurement is inexact, since the main component measured using a filter which passes only this band, is diffuse reflection from the surface of the printed colorant layer.

In a preferred embodiment of the invention, an "incorrect" filter is used in the measurement of OD, whenever the filter usually used (i.e., that is matched to the colorant) blocks almost all the light that passes through the colorant (i.e., the system is in saturation).

In general three color filters and a filter for black are used in measurement, namely a yellow filter (which passes only light absorbed by the yellow colorant and which is the "correct" filter for measuring OD of the yellow colorant); a cyan filter (which passes only light absorbed by the cyan ink and which is the "correct" filter for measuring OD of the cyan colorant) and a magenta filter (which passes only light absorbed by the magenta ink and which is the "correct" filter for measuring OD of the cyan colorant). A broadband filter is used for black. Since, when the colorant is near saturation (defined as where the diffuse reflection from the surface of the colorant, which amount is dependent on the gloss of the colorant is comparable to that of the light reflected through the colorant), measurements made with the "correct" filter are not correctly affected by the colorant thickness, another filter is used to determine the thickness (by equivalent OD).

In a preferred embodiment of the invention, the filter to be used for measuring the OD is chosen based on its meeting two criteria. First it must not produce a saturation or near saturation condition. Since the spectra of the filters include spectral regions which have little absorption by the particular process color ink, this is seldom a problem for any filter except the "correct" one, for process colors. The second criteria is that the expected OD to be measured when using the filter be a maximum as compared to that measured by the other two filters. Thus, when a given colorant (as printed) when measured with its correct filter, is not in saturation, the "correct" filter is used, since it all the filters meet the first criteria and the correct filter best meets the second criteria. However, when using the first filter results in saturation or near saturation, another filter, which best meets the second criteria is used.

For special inks, more than one filter may provide saturated measurements. In this case, the filter that provides unsaturated measurements is used. If none are in saturation, the measurement utilizing the highest OD is used.

In a preferred embodiment of the invention, tables which translate measured OD utilizing an "incorrect" filter to actual OD of the colorant being measured are derived either from actual measurements or from calculations based on the band pass of the various filters and on the spectra of the colorants, which, for process colors, are standardized and for special colors can be computed from the mixtures used.

In accordance with a preferred embodiment of the invention, tables are prepared or recommended measurements of OD are determined for various ODs of the process colors when the "incorrect" filter is used. The increased ODs can be measured in at least three ways.

Whenever a printed layer is believed by a user to be in saturation the "incorrect" filter and corresponding table would be used.

In a digital (and in some other computer controlled) printing systems, where the OD measurement is made by an operator, the tables are stored in a computer associated with the printer. For each color believed to be near saturation, the computer recommends the use of a best "incorrect" filter and gives a target value of "OD" as the target value for measurement with the "incorrect" filter.

It should be understood that as a practical measure software for carrying out the present invention may be supplied in the form of software on a suitable recording medium such as a diskette or CD ROM or for downloading (using the web or by direct transfer) or in the form of patch on existing software.

Where an in-line OD measurement is made in a digital of other computer controlled printer, the printer automatically determines the best filter that meets the above mentioned criteria and uses that filter and the above mentioned tables to determine the OD.

As used herein, the terms "comprise", "include" and "have" and their conjugates mean "including but not necessarily limited to".

While the invention has been described with reference to best mode embodiments, it should be understood that these embodiments are exemplary only and are not meant to act as limitations on the scope of the invention, which is defined by the accompanying claims. In addition each of the embodiments of the invention is described with reference to certain features. These features may be combined in additional preferred embodiments of the invention and some preferred embodiments of the invention may omit certain features of the described embodiments.

What is claimed is:

1. A method of determining an adjusted color to be used for computing colorants for printing on a specified substrate, comprising:
   specifying an apparent color;
   estimating diffuse reflection from an outside surface of colorants when printed on the specified substrate; and
   adjusting the specified color for the effects of the estimated diffuse reflection to determine a color to be used for computing the colorants.

2. A method according to claim 1 wherein the specified color is a color spectrum.

3. A method according to claim 1 wherein the specified apparent color is determined from a measurement of a printed exemplar.

4. A method according to claim 2 and including determining a mixture of colorants based on the adjusted spectrum.

5. A method according to claim 4, including:
   printing the mixture of colorants as separate separations on the substrate.

6. A method according to claim 5 wherein the separations are printed as half-tone configurations.

7. A method according to claim 5 wherein the colorants comprise at least one process color.

8. A method according to claim 5 wherein determining the mixture of color components comprises determining a percent coverage of the colorants of the separations substrate.

9. A method according to claim 5 and including correcting the estimate of diffuse reflection based on a percent coverage of the substrate by the colorants and repeating the determination of the color mixture based on the corrected estimate.

10. A method according to claim 4 and including printing the mixture of colorants as a single layer of mixed colorant.

\* \* \* \* \*

UNITED STATES PATENT AND TRADEMARK OFFICE
CERTIFICATE OF CORRECTION

PATENT NO. : 6,784,994 B1
DATED : August 31, 2004
INVENTOR(S) : Eli Kritchman et al.

Page 1 of 1

It is certified that error appears in the above-identified patent and that said Letters Patent is hereby corrected as shown below:

Column 10,
Line 3, after "separations" add -- on the --

Signed and Sealed this

Fifth Day of April, 2005

JON W. DUDAS
*Director of the United States Patent and Trademark Office*